United States Patent [19]

Kollmeyer

[11] 4,053,619

[45] Oct. 11, 1977

[54] 2-SUBSTITUTED-2-(ACETOXYETHYL) ESTERS OF (1-METHYL-2-IMIDAZOLIDINYLIDENE) NITROACETIC ACID

[75] Inventor: Willy D. Kollmeyer, Modesto, Calif.

[73] Assignee: Shell Oil Company, Houston, Tex.

[21] Appl. No.: 773,452

[22] Filed: Mar. 2, 1977

[51] Int. Cl.$^2$ .................. C07D 233/26; A61K 31/415
[52] U.S. Cl. ................................. 424/273 R; 548/342
[58] Field of Search ...................... 260/309.7; 424/273

[56] References Cited

U.S. PATENT DOCUMENTS 3,948,934  4/1976  Tieman et al. .................... 260/309.7

OTHER PUBLICATIONS

Meyer et al., Chem. Abst. 1973, vol. 79, No. 146519d.
Wennerbeck Acta Chem. Scand., 1973, vol. 27, pp. 258–270.

*Primary Examiner*—Natalie Trousof

[57] ABSTRACT

Insecticidal 2-substituted-2-(acetoxyethyl) esters of (1-methyl-2-imidazolidinylidene)nitroacetic acid.

4 Claims, No Drawings

2-SUBSTITUTED-2-(ACETOXYETHYL) ESTERS OF (1-METHYL-2-IMIDAZOLIDINYLIDENE) NITROACETIC ACID

DESCRIPTION OF THE INVENTION

It has been found that useful insecticidal activity is possessed by certain 2-substituted-2-(acetoxyethyl) esters of (1-methyl-2-imidazolidinylidene)nitroacetic acid. These compounds are described by the formula:

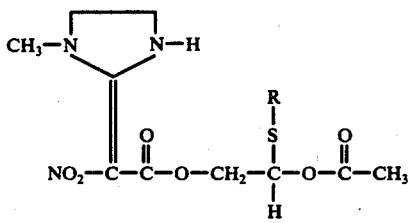

(I)

wherein R is alkyl of one to four carbon atoms, or is phenyl or phenyl substituted by from one to three halogen atoms or by one of nitro, cyano, alkyl, mono- and polyhaloalkyl, alkoxy or alkylthio, wherein the alkyl moiety contains from one to six carbon atoms. By halogen is meant chlorine, bromine, iodine and fluorine — bromine, chlorine and fluorine being preferred. Suitably, each alkyl moiety is of straight-chain or branched-chain configuration; methyl is preferred.

For illustration, preparation of typical individual species of the genus are described in the examples included hereinafter. Other typical, illustrative species of this genus include those wherein R is:
ethyl
isopropyl
4-(trifluoromethyl)phenyl
4-(methylthio)phenyl
4-nitrophenyl
2-chlorophenyl
2-methylphenyl
2,4-dichlorophenyl
2,4,5-trichlorophenyl Compounds of the invention can be prepared by a three or four stage process wherein a methyl or ethyl ester of (1-methyl-2-imidazolidinylidene)nitroacetic acid (A) of the formula

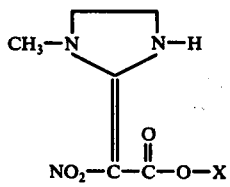

wherein X is methyl or ethyl is treated to alter the ester moiety, R, as follows:

a. A is treated with the alcohol, R—S—CH$_2$—CH$_2$—OH, X being changed to —CH$_2$—CH$_2$—S—R, giving intermediate B.

b. B is treated with sodium periodate to oxidize the sulfur, —CH$_2$—CH$_2$—S—R becoming —CH$_2$—CH$_2$—S(O)—R, giving intermediate C.

c. C is treated with acetic anhydride, to effect a Pummerer Reaction, —CH$_2$—CH$_2$—S(O)—R becoming

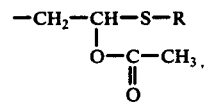

i.e. the desired compound of the invention.

In some cases the hydrogen atom on the ring nitrogen atom is replaced by an acetyl moiety; in such a case, this intermediate is treated with a mild base, such as sodium bicarbonate, to remove the acetyl moiety from the ring nitrogen atom, to give the desired compound of the invention.

Example 1, hereinafter, describes a method for preparing the alkyl ester starting materials, from a 1-alkyl-imidazolidine-2-thione (McKay et al., J. Org. Chem., 22, 1581 (1957).

Step (a) can be conducted by treating the alkyl ester with at least two equivalents of an alkali metal alcoholate of the alcohol R—S—CH$_2$—CH$_2$—OH, in a solvent such as dimethylformamide. This may be done by treating the alcohol in the solvent with an alkali metal hydride, then adding the ester, also in the solvent. The reaction of the alcohol and hydride usually is exothermic so that cooling is usually needed to control the temperature of the reaction mixture. Reaction of the alcoholate with the ester ordinarily can be conducted at or somewhat above room temperature. Recovery of the product is effectively attained in most cases by quenching the final reaction mixture in water, treating the aqueous mixture with a suitable solvent such as esther to remove the solvent alcohol and other neutral organic species, then acidifying the aqueous phase. In some cases, the product ester crystallizes out of the water; in other cases, it can be recovered by extracting the water-phase with a suitable water-insoluble solvent such as methylene chloride or ethyl ether.

The alcohols, R—S—CH$_2$—CH$_2$—OH are a known class of compounds, some wherein R is phenyl being disclosed by Schultz et al., Journal of Organic Chemistry, 28, 1140-1142 (1963).

The step (b) oxidation can be conducted by treating intermediate B, in solution in a solvent such as a mixture of water and acetone, with an equivalent or small excess of the sodium periodate. The treatment conveniently is conducted at room temperature. The desired product can be isolated by filtering the crude reaction mixture and stripping the solvent from the filtrate. The product can be purified by crystallization and/or chromatographic techniques.

The Pummerer Reaction of step (c) can be conducted by treating intermediate C with an excess of acetic anhydride at a moderately elevated temperature — conveniently at the reflux temperature. The desired product can be recovered from the crude reaction mixture by stripping the excess anhydride. If an N-acetyl linkage is found it can be cleaved by treatment with sodium bicarbonate after stripping of the excess acetic anhydride. The product can be purified by chromatographic and/or crystallization techniques.

In cases where the product obtained on stripping of the excess anhydride is acetylated at the ring nitrogen atom, the acetyl moiety can be removed by dissolving the product in a suitable solvent, such as methanol, and treating the solution with a mild base, such as sodium bicarbonate. The treatment can be conducted at room temperature. The desired product can be recovered and purified by removing the solvent, treating the residue with water and a water-immiscible solvent, such as methylene chloride, separating the organic phase, stripping the solvent and separating the product from the residue by extraction techniques and purifying it by crystallization techniques.

The procedures for preparing compounds of this invention are illustrated in the following examples of the preparation of particular species of such compounds. In all cases the identity of the precursor (s) was established and the identity of the final product was confirmed, by appropriate analyses.

EXAMPLE 1
(1-methyl-2-imidazolidinylidene)nitroacetic acid, 2-(acetyloxy)-2-(methylthio)ethyl ester (1)

360 g of dimethyl sulfate was added dropwise to a stirred and refluxing suspension of 332 g of 1-methylimidazolidine-2-thione in 900 ml of hexane. After 2 hours further stirring at the same temperature, the mixture was cooled and treated with 114 g of sodium hydroxide in 320 ml of water. The hexane layer was separated and dried (MgSO$_4$). The aqueous layer was extracted with methylene chloride and the extract was dried (MgSO$_4$). The solvents were evaporated under reduced pressure and the combined residues were distilled to give 1-methyl-2-(methylthio)-2-imidazoline (1A) as a colorless liquid, b.p.: 50°-52° at 0.02 Torr.

35.7 g methyl nitroacetate was added slowly to a refluxing mixture of 39.0 g of 1A and 300 ml of isopropyl alcohol. The mixture then was refluxed for 1 hour with provision to remove the methyl mercaptan by-product. The mixture was cooled and filtered to give the methyl ester of (1-methyl-2-imidazolidinylidene)nitroacetic acid (1B) as a solid, m.p.: 214°-217° (with decomposition).

4.02 g of 1B, 35 g of 2-(methylthio)ethanol, 2.2 g of 45% sodium hydride in mineral oil, and 25 ml of dry dimethylformamide were mixed and the mixture was stirred overnight at room temperature. The mixture then was poured into water and extracted with methylene chloride. 5 ml of acetic acid was added to the aqueous layer, which was then extracted with methylene chloride. The latter extract was dried (MgSO$_4$) and the solvent was evaporated to give a light yellow oil, which was triturated with a mixture of petroleum ether and ethyl acetate. Filtration gave a white powder, which was recrystallized from petroleum ether/methylene chloride to give the 2-(methylthio)ethyl ester of (1-methyl-2-imidazolidinylidene)nitroacetic acid (1C), as a colorless solid, m.p.: 129°-131°.

13.89 g of sodium metaperiodate was slowly added to a mixtue of 17.02 g of 1C, 80 ml of acetone and 80 ml of water at room temperature. The resulting mixture was stirred for 3 hours at room temperature and filtered. The filtrate was stripped of solvent and the residue was recrystallized from ethanol to give the 2-(methylsulfinyl)ethyl ester of (1-methyl-2-imidazolidinylidene)nitroacetic acid, as a white powder (1D), m.p.: 148°-151°.

11.1 g of 1D was mixed with 100 ml of acetic anhydride and the mixture was refluxed for 4 hours. The excess anhydride was stripped and the residue was column chromatographed over silica gel using a 50:50 (v/v) mixture of acetone and hexane as eluent. The product was recrystallized from chloroform: petroleum ether to give 1, as a yellow powder, m.p.: 157°-160°.

EXAMPLE 2
(1-methyl-2-imidazolidinylidene)nitroacetic acid, 2-(acetyloxy)-2-(phenylthio)ethyl ester (2)

The ethyl ester of (1-methyl-2-imidazolidinylidene)nitroacetic acid (2A), was prepared, as pale cream colored crystals, m.p.: 154°-156°, from ethyl nitroacetate, according to the procedure described in Example 1 for preparing the methyl ester of that acid (1B).

A mixture of 4.3 g of 2A, 30.85 g of 2-(phenylthio)ethanol, 1.71 g of 56% sodium hydride in mineral oil and 25 ml of dimethylformamide was stirred at room temperature for 17 hours, then at 50°-60° for 3 hours. Then the solvent was stripped under reduced pressure, the residue was diluted with water and the mixture was extracted with methylene chloride. The extract phase was dried (MgSo$_4$), and stripped of solvent. The residue was triturated with a mixture of ethyl acetate and petroleum ether to give a powder, which was recrystallized from ethyl acetate to give the 2-(phenylthio)ethyl ester of (1-methyl-2-imidazolidinylidene)nitroacetic acid (2B), as a white solid, m.p.: 128°-130° (with evolution of gas).

11.32 g of 2B, 8.56 g of sodium metaperiodate, 100 ml of acetone and 100 ml of water were mixed and the mixture was stirred for 18 hours at room temperature. The mixture was filtered. The filtrate was stripped of solvent, the resulting solid residue was partially dissolved in hot ethanol, and the mixture was filtered. Ether was added to the filtrate, and the solid that formed was collected, being the 2-(phenylsulfinyl)ethyl ester of (1-methyl-2-imidazolidinylidene)nitroacetic acid (2C) white crystals, m.p.: 127°-128°.

12.78 g of 2C was mixed with 200 ml of acetic anhydride and the mixture was refluxed for 4 hours. Then the excess anhydride was stripped. The residue was dissolved in methanol. The solution was treated with 3.11 g of sodium bicarbonate in 100 ml of water for 24 hours at room temperature. The solvent was stripped under reduced pressure. The residue was treated with a mixture of 200 ml of water and 200 ml of methylene chloride. The phases were separated and the water phase was extracted with methylene chloride. The methylene chloride solutions were combined, dried (MgSO$_4$), and the solvent was stripped. The residue was triturated with a mixture of ethyl acetate and petroleum ether. The residue was decolorized with charcoal and recrystallized from ethyl acetate to give 2, as white crystals, m.p.: 128°-131° (with gas evolution).

Compounds of this invention exhibit useful insecticidal activity, being of particular interest for control of the larvae "caterpillar" or "worm" forms of insects of the genus Heliothis, such as *H. zea* (corn earworm, cotton bollworm, tomato fruitworm), *H. virescens* (tobacco budworm); the genus Agrotis, such as *A. ipsilon* (black cutworm); the genus Trichoplusia, such as *T. ni* (cabbage looper), and the genus Spodoptera, such as *S. littoralis* (Egyptian cotton leafworm). In tests that have been conducted they have exhibited low, or no, toxicity to other insects such as aphids, houseflies, the 2-spotted spider mite and mosquito larva.

Activity of compounds of this invention with respect to insects was determined by using standardized tests to establish the LC$_{50}$ dosage (in milligrams of test compound per 100 milliliters of solvent or liquid carrier required in the solution or suspension of test compound used) to kill 50% of the test insects. The test insects were the housefly, corn earworm, pea aphid and 2-spotted spider mite. Activity with respect to mosquito larvae was determined by placing the larvae in water containing the test compound.

Compounds 1 and 2 were found to be inactive with respect to the houseflies and mites, slightly active with respect to mosquito larvae, and active with respect to the corn earworms. Compound 1 was slightly active and Compound 2 was inactive with respect to the aphids.

The invention includes within its scope insecticidal compositions comprising an adjuvant — that is, a carrier, optionally a surface-active agent — and, as active ingredient, at least one insecticide of this invention. Likewise the invention includes also a method of combatting insect pests at a locus which comprises applying to the locus an effective amount of at least one insecticide of the invention.

The term "carrier" as used herein means a material which may be inorganic or organic and of synthetic or natural origin with which the active compound is mixed or formulated to facilitate its application to the plant, seed, soil or other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example, superphosphates.

Suitable liquid carriers include solvents for the salts of this invention and liquids in which the toxicant is insoluble or only slightly soluble.

Examples of such solvents and liquid carriers generally are water, alcohols, for example, isopropyl alcohol; ketones, such as acetone, methyl ethyl ketone, methyl isobutyl ketone and cyclohexanone; ethers; aromatic hydrocarbons such as benzene, toluene and xylene; petroleum fractions, such as kerosene, light mineral oils; chlorinated hydrocarbons, such as carbon tetrachloride, perchlorethylene, trichloroethane; including liquefied normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkyl- amines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbons atoms in the molecule, for example, sodium lauryl sulfate, sodium secondary alkyl sulfates, sodium salts of sulfonated caster oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75%w of toxicant and usually contain, in addition to solid carrier, 3–10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing $\frac{1}{2}$–10%w of active ingredient. Granules may be manufactured by agglomeration or impregnation techniques. Generally, granules will contain $\frac{1}{2}$–25%w active ingredient and 0–10%w of additives such as stabilizers, slow release modifiers and binding agents. Emulsifiable concentrates usually contain, in addition to the solvent, and when necessary, co-solvent, 10–50%w/v active ingredient, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%w active ingredient, 0–5%w of dispersing agents, 0.1–10% w of suspending agents such as protective colloids and thixotropic agents, 0–10% w of appropriate additives such as defoamers, corrosion inhibitors, stabilizers, penetrants and stickers, and as carrier, water or an organic liquid in which the active ingredient is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of active ingredient at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of the active ingredient at the locus being within the skill of those versed in the art. In general, however, the effective dosage of compounds of this invention at the locus to be protected — i.e. the dosage to which the insect contacts — is of the order of 0.001% to 0.5% based on the total weight of the formulation, though under some circumstances the effective concentration will be as little as 0.001% or as much as 2%, on the same basis.

I claim:

1. A compound of the formula:

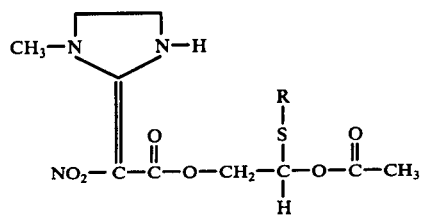

wherein R is alkyl of one to four carbon atoms, or is phenyl or phenyl substituted by from one to three halogen atoms or by one of nitro, cyano, alkyl, mono- and polyhaloalkyl, alkoxy or alkylthio, wherein the alkyl moiety contains from one to six carbon atoms.

2. A compound according to claim 1 wherein R is methyl.

3. An insecticidal composition comprising an insecticidally effective amount of a compound of claim 1 together with a carrier, optionally a surface-active agent.

4. A method for killing insects which comprises contacting them with a lethal dosage of a compound of claim 1.

* * * * *